United States Patent [19]

Warder et al.

[11] Patent Number: 4,872,563
[45] Date of Patent: Oct. 10, 1989

[54] PROTECTIVE ENCLOSURE FOR HAZARDOUS MATERIAL PRIMARY CONTAINERS

[75] Inventors: William G. Warder, Weston, Mo.; David R. Frye, Longview, Tex.

[73] Assignee: Pro-Tech-Tube, Inc., Weston, Mo.

[21] Appl. No.: 200,568

[22] Filed: May 31, 1988

[51] Int. Cl.⁴ ............................................. B65D 17/00
[52] U.S. Cl. .................................... 206/634; 220/454; 604/403; 422/102
[58] Field of Search ............... 220/265, 270, 307, 410, 220/453, 454, 457; 206/523, 601, 634, 446, 204, 205; 604/403; 422/102, 104

[56] References Cited

U.S. PATENT DOCUMENTS

| | | | |
|---|---|---|---|
| 597,726 | 1/1898 | Lovell | 206/446 X |
| 2,283,867 | 5/1942 | Flosdorf et al. | 206/634 X |
| 3,401,791 | 9/1968 | Stott et al. | 206/204 |
| 3,613,874 | 10/1971 | Miller | 206/620 X |
| 4,240,547 | 12/1980 | Taylor | 206/523 X |

*Primary Examiner*—John Fox
*Attorney, Agent, or Firm*—Kokjer, Kircher, Bradley, Wharton, Bowman & Johnson

[57] ABSTRACT

This invention relates to a method and device for transporting hazardous materials, especially materials such as biological samples contained in vials. The device comprises an enclosure having a top that locks onto a body section so as to substantially preclude removal of the top after it is in place on the body. The body section includes a tab which can be grasped and pulled along a line of weakness to rip open the device once it reaches its destination. The inside of the enclosure including the top is lined with a resilient material along with a moisture impervious outer liner. The resilient material is preferably highly liquid absorbing and is impregnated with a germicidal/pesticidal substance so that in the unlikely event the container breaks its contents will be absorbed and contained within the protective enclosure.

9 Claims, 1 Drawing Sheet

PROTECTIVE ENCLOSURE FOR HAZARDOUS MATERIAL PRIMARY CONTAINERS

BACKGROUND AND SUMMARY OF THE INVENTION

This invention relates generally to shipping containers and, more particularly, to a method and device for safely packaging and shipping hazardous materials, especially biological infectious substances ad radioactive samples.

While government regulations specifiy standards for shipment of explosives, flammables, radioactive materials and other hazardous chemicals, there are presently no regulations regarding shipping of biological specimens such as blood, urine or other body fluids which are commonly analyzed for medical diagnostic purposes. Thus, these materials may be shipped through the mail and by private carriers without restriction. While only occasionally does a shipping container break, the consequences of a breakge of the primary container for the hazardous material can be catastrophic for unknowledgeable and unprotected individuals who are handling it.

The present invention addresses the need for safely transporting hazardous materials by providing a method and device which greatly reduces the chance of damage to the primary container for the hazardous material during shipment and also greatly reduces the risk of exposure to the hazardous material if the container is damaged.

It is therefore a primary object of the present invention to provide a method and device for transporting hazardous materials, especially infectious substances and biological specimens.

As a corollary to the foregoing objective, an important aim of the invention is to provide a method and device of transporting hazardous material which protects the primary container for the material against breakge during shipment.

Another corollary to the object above stated is to provide a method and device which protects those who handle hazardous materials during shipping from exposure to danger if the primary container for the hazardous material does break.

Another object of the invention is to provide a method and device for transporting primary containers of hazardous materials wherein the device is designed to destruct upon opening thereby assuring that it cannot be used more than one time.

It is also an important aim of our invention to provide a method and device which assures the integrity of samples obtained in random and blind testing of workers, athletes and racing animals by assuring that a container for such a sample cannot be the subject of tampering during shipment without giving a visible indication that tampering has occurred.

Another one of the objects of this invention is to provide a method and device of the type described which may include a shock warning device so as to provide an immediate indication if the transporting package has received a dangerously high shock during shipping.

It is also an important one of the objectives of our invention to provide a method and device of the type described wherein a plurality of the devices can be serially numbered to enhance tracking during shipment.

A further but by no means final objective of the invention is to provide a method and device of the type described wherein a shipping container may be constructed to house a single primary container of hazardous material or multiple primary containers of hazardous material as the need may dictate.

Other objectives of our invention will be apparent from the following description and claims when read in light of the accompanying drawing:

Figure 1:
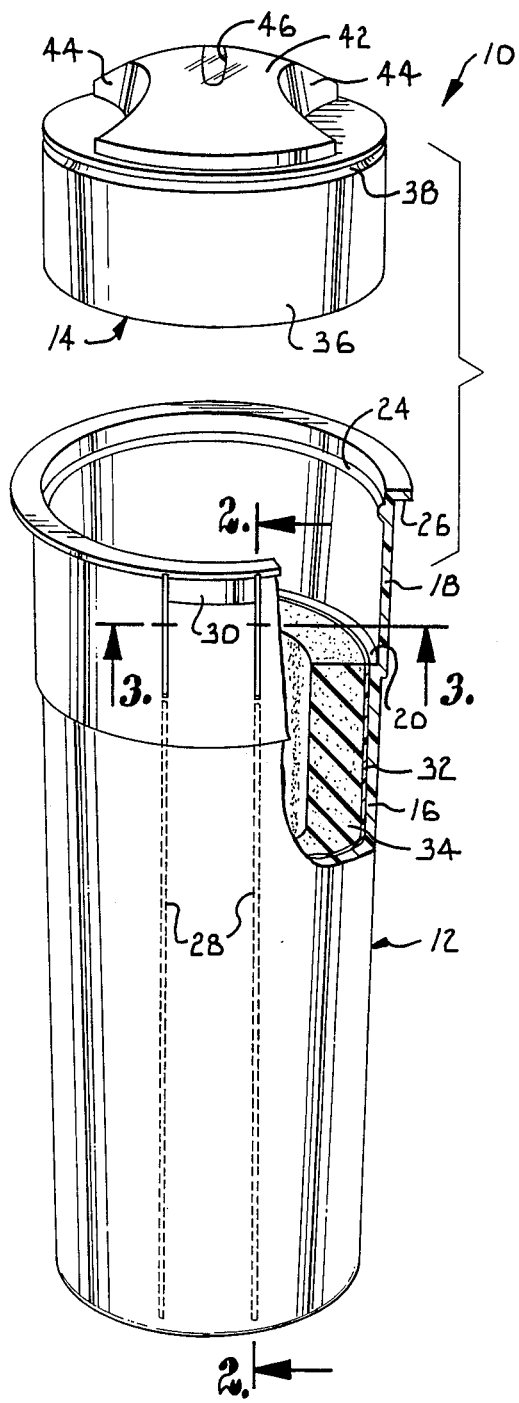
FIG. 1 is an exploded perspective view of the shiping device of the present invention.

Referring initially to FIG. 1, the device of the present invention is designated generally by the numeral 10 and includes a generally cylindrical enclosure 12 and a complimental top 14. Enclosure 12 includes an elongated generally cylindrical main body section 16 of a first diameter and an integral top body section 18 of a somewhat larger diameter than first section 16. The point of juncture between body sections 16 and 18 presents a ledge 20 on the inside of the enclosure. Manifestly, sections 16 and 18 present a continuous sidewall of enclosure 12. An integral bottom section 22 is visible in FIG. 2 and is generally planar so as to present a flat bottom surface.

Spaced downwardly a short distance from the uppermost edge of top body section 18 is a circumferentially extending detent 24 the purpose of which will be described hereinafter. Section 18 terminates in an outwardly extending tip 26 which extends around the entire circumference of the top. As noted in FIG. 1, enclosure 12 is provided with two vertically extending lines of weakness 28, each of which is designed in the drawing by closely spaced parallel broken lines. Integrally formed into top body section 18 in the area between lines of weakness 28 is a tab 30 which is positioned beneath lip 26. By virtue of extending outwardly at least as far as tab 30, lip 26 offers protection against accidental opening of the tab during shipment.

The inside of body section 16 is lined with a water impervious liner 32 made of polyethylene or other suitable material. Spaced further inwardly from body section 16 on the inside of water impervious liner 32 is a resilient layer 34 of foam rubber or other cushioning type of material.

Top 14 includes a cylindrical sidewall 36 which is of a diameter to be received by top body section 18 and to this end includes a channel 38 which extends around the circumference of sidewall 36 and receives detent 24 in locking relationship. Top 14 includes a top planar section 40 which in turn supports a rounded dome section 42 characterized by indentations 44 which present gripping surfaces for the fingers of a user. A small cutaway section 46 in the top of the dome section 42 provides an area for locating a shock exposure indicator of a type well known to those skilled in the art but not shown in the drawings in the interest of brevity.

Figure 2:
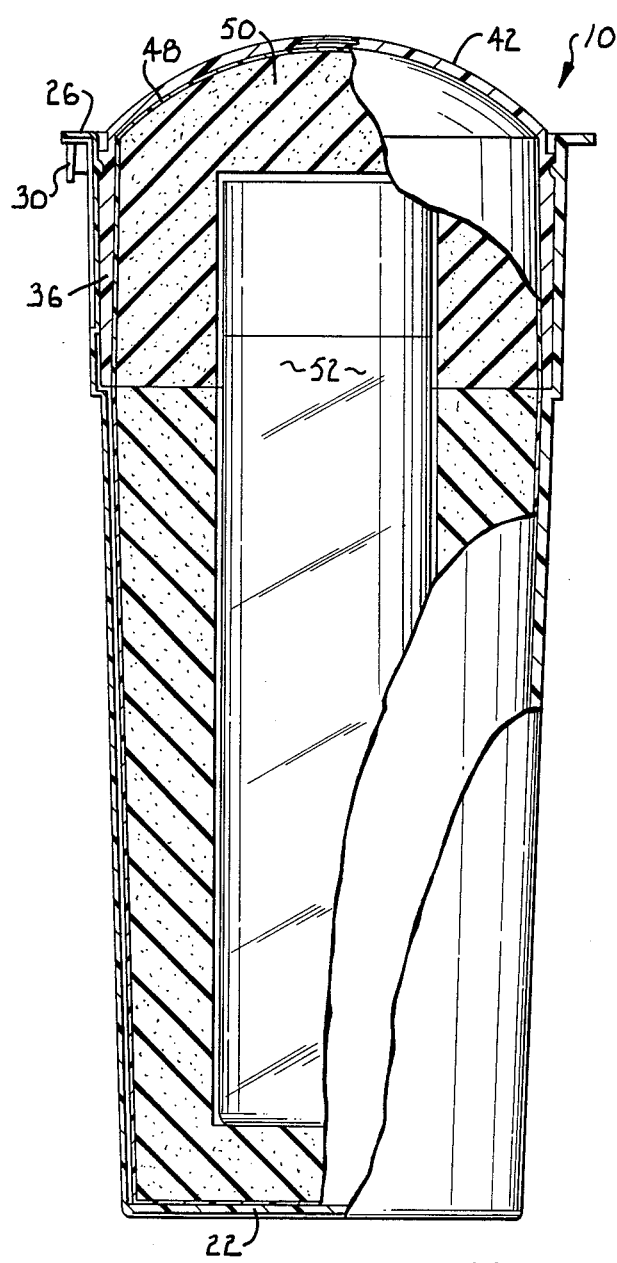
FIG. 2 is a vertical cross sectional view, with portions shown in elevation, and taken along the line 2—2 of FIG. 1.
Figure 3:
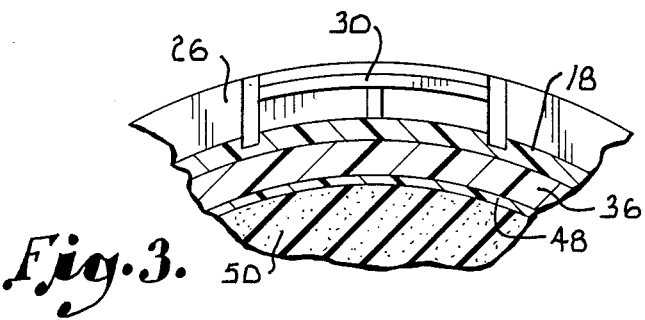
FIG. 3 is a horizontal cross sectional view looking in the direction of arrows 3'3 of FIG. 1.

With reference to FIG. 2, the inside of top 14 is lined with a water impervious liner 48 constructed of the same material as liner 32. On the inside of liner 48 is a layer 50 of resilient material which may be the same material as layer 34.

In use, the device 10 is utilized to hold a primary container such as stoppered vial 52 illustrated in FIG. 2.

Vial 52 may contain any one of a number of hazardous materials, especially biological fluids. Once the vial is positioned within the cavity formed by resilient layer 34, top 14 is positioned inside of body section 18 until the lowermost edge of top 14 rests on ledge 20. As the top 14 is so positioned, detent 24 will be received in channel 38 thus substantially impeding any effort to manually remove top 14.

The resilient layers 34 and 50 substantially cushion vial 52, thus precluding breakage of the vial. In the event that a break does occur, however, moisture impervious liners 32 and 48 substantially preclude escape of liquid from the device. Also, it is desirable to impregnate resilient layers 34 and 50 with a germicidal/pesticidal substance as circumstances dictate which will kill pathogens that escape from the vial into the interior of the device. If a radioactive device is being shipped in the device 10 it may be desirable to utilize an inner liner which is capable of shielding radiation in place of liners 32 and 48.

Once the device 10 reaches it destination, tab 30 is grasped by a technician and pulled outwardly so as to break open the side of enclosure 12 along the length of the latter. This provides sufficient access to the interior of the device so as to allow removal of top 14 and then vial 52. This assures that the device 10 cannot be reused thereby eliminating any possibility of a contaminated device 10 being used to ship hazardous materials and assuring that the device will provide visible evidence of tampering. As aforementioned, a shock indicator may be placed in cutaway section 46 so as to provide an immediate warning signal of a possible damage container within the enclosure in the event that the device 10 has been subjected to forces of a magnitude that are likely to cause breakage. It is, of course, to be be understood that it is within the scope of the invention to form a unitary assembly where a plurality of the devices 10 would be joined together so as to present a single device which could ship a large number of containers of hazardous material in a single package.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, we claim:

1. A device for transporting a container of hazardous material, said device comprising:
   an enclosure having a bottom and a side wall;
   top means for closing said enclosure;
   means for locking said top means to said side wall so as to impede removal of said top means once the latter is in its closing position on said enclosure;
   resilient means lining the interior of said enclosure and said top and presenting a cavity for receiving the container, said resilient means being impregnated with a germicidal agent;
   said side wall presenting a line of weakness extending along the side wall; and
   means coupled with said side wall in close proximity to said line of weakness and extending outwardly from said side wall and presenting a tab which can be pulled by a user of said device to open said enclosure.

2. A device as set forth in claim 1, wherein said sidewall presents a second line of weakness parallel to and substantially coextensive in length with the first mentioned line of weakness and wherein said tab presenting means extends from said sidewall at a location between the first and second lines of weakness.

3. A device as set forth in claim 1, wherein is included a moisture impervious liner on the side of said vertical means which is adjacent said enclosure and said top means.

4. A method of packaging for transport a hazardous material which is held in a container, said method comprising the steps of:
   enclosing said container within an enclosure device characterized by a line of weakness along one side and tab means projecting from said side in close proximity to said line of weakness;
   cushioning said container with a resilient liner disposed between the container and the enclosure device;
   impregnating said resilient liner with a germicidal/pesticidal agent; and
   placing the top on said enclosure in a manner so as to substantially impede its removal; and
   whereby when said container is to be removed from said device said tab means may be pulled thereby destroying said device while opening it to accommodate removal of said container.

5. A method as set forth in claim 4, wherein said enclosure is characterized by a second line of weakness parallel to and substantially coextensive in length with the first mentioned line of weakness and wherein said tab means projects from said side at a location between said first and second lines of weakness.

6. A method as set forth in claim 5, wherein is included a moisture impervious liner on the side of said resilient liner which is adjacent said enclosure.

7. A protective device for packaging a container holding hazardous materials such as those containing viable microorganisms, said device comprising:
   an enclosure having a bottom and a side wall which presents a top section of the enclosure having a size to receive and hold said container therein;
   a top for said enclosure, said top being separate from the enclosure and having a size and shape to be inserted into said top section to close the enclosure and enclose the container therein;
   means for locking said top in said top section to impede removal of the top therefrom;
   a line of weakness on said side wall; and
   means for providing a tab on the side wall in proximity of said line of weakness, said tab being accessible for pulling to break the side wall along said line of weakness in a manner to effect release of said locking means and allow removal of the top to provide access to the container.

8. A device as set forth in claim 7, wherein said locking means comprises cooperating detent means on said side wall and top.

9. A device as set forth in claim 7, including resilient means lining the interior of said enclosure and presenting a cavity for receiving the container, said resilient means being impregnated with a germicidal agent.

* * * * *